United States Patent
Freeberg

(10) Patent No.: US 8,160,704 B2
(45) Date of Patent: Apr. 17, 2012

(54) SYSTEM AND METHOD FOR ENABLING RELAYED COMMUNICATIONS BY IMPLANTABLE MEDICAL DEVICES

(75) Inventor: Scott Freeberg, Birchwood Village, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1073 days.

(21) Appl. No.: 11/265,618

(22) Filed: Nov. 2, 2005

(65) Prior Publication Data

US 2007/0100396 A1 May 3, 2007

(51) Int. Cl.
*A61N 1/00* (2006.01)

(52) U.S. Cl. ............... 607/32; 607/30; 607/60

(58) Field of Classification Search .......... 607/30, 607/32, 60
See application file for complete search history.

(56) References Cited

U.S. PATENT DOCUMENTS

| | | | |
|---|---|---|---|
| 4,799,059 A * | 1/1989 | Grindahl et al. | 340/870.03 |
| 5,683,432 A * | 11/1997 | Goedeke et al. | 607/32 |
| 5,843,139 A * | 12/1998 | Goedeke et al. | 607/32 |
| 6,223,083 B1 * | 4/2001 | Rosar | 607/60 |
| 6,349,234 B2 * | 2/2002 | Pauly et al. | 607/60 |
| 6,381,492 B1 * | 4/2002 | Rockwell et al. | 607/5 |
| 6,472,991 B1 * | 10/2002 | Schulman et al. | 340/995.1 |
| 6,482,154 B1 * | 11/2002 | Haubrich et al. | 600/300 |
| 6,631,296 B1 * | 10/2003 | Parramon et al. | 607/61 |
| 6,897,788 B2 * | 5/2005 | Khair et al. | 340/870.16 |
| 6,959,217 B2 * | 10/2005 | DelMain et al. | 607/60 |
| 6,993,393 B2 * | 1/2006 | Von Arx et al. | 607/60 |
| 7,110,823 B2 * | 9/2006 | Whitehurst et al. | 607/60 |
| 7,110,824 B2 * | 9/2006 | Amundson et al. | 607/60 |
| 7,209,790 B2 * | 4/2007 | Thompson et al. | 607/60 |
| 7,225,030 B2 * | 5/2007 | Kroll et al. | 607/60 |
| 7,539,489 B1 * | 5/2009 | Alexander | 455/423 |
| 2001/0012955 A1 * | 8/2001 | Goedeke et al. | 607/27 |
| 2002/0123672 A1 * | 9/2002 | Christophersom et al. | 600/300 |
| 2002/0143372 A1 * | 10/2002 | Snell et al. | 607/30 |
| 2002/0183806 A1 * | 12/2002 | Abrahamson et al. | 607/60 |
| 2003/0009204 A1 * | 1/2003 | Amundson et al. | 607/60 |
| 2003/0097157 A1 * | 5/2003 | Wohlgemuth et al. | 607/27 |
| 2003/0114897 A1 * | 6/2003 | Von Arx et al. | 607/60 |
| 2003/0149459 A1 * | 8/2003 | Von Arx et al. | 607/60 |
| 2003/0187484 A1 * | 10/2003 | Davis et al. | 607/60 |
| 2003/0220673 A1 * | 11/2003 | Snell | 607/60 |
| 2003/0229383 A1 * | 12/2003 | Whitehurst et al. | 607/60 |
| 2004/0064166 A1 * | 4/2004 | Thompson et al. | 607/60 |
| 2004/0122477 A1 * | 6/2004 | Whitehurst et al. | 607/9 |
| 2004/0127958 A1 * | 7/2004 | Mazar et al. | 607/60 |
| 2004/0127959 A1 * | 7/2004 | Amundson et al. | 607/60 |
| 2004/0158299 A1 * | 8/2004 | Patrias | 607/60 |
| 2004/0167587 A1 * | 8/2004 | Thompson | 607/60 |
| 2004/0176811 A1 * | 9/2004 | Von Arx et al. | 607/32 |
| 2004/0176822 A1 * | 9/2004 | Thompson et al. | 607/60 |
| 2006/0161222 A1 * | 7/2006 | Haubrich et al. | 607/60 |
| 2006/0161223 A1 * | 7/2006 | Vallapureddy et al. | 607/60 |
| 2006/0247736 A1 * | 11/2006 | Roberts | 607/60 |
| 2007/0135855 A1 * | 6/2007 | Foshee et al. | 607/31 |
| 2007/0153705 A1 * | 7/2007 | Rosar et al. | 370/254 |
| 2007/0167995 A1 * | 7/2007 | Dudding et al. | 607/60 |
| 2007/0167996 A1 * | 7/2007 | Dudding et al. | 607/60 |
| 2007/0185550 A1 * | 8/2007 | Vallapureddy et al. | 607/60 |
| 2007/0239229 A1 * | 10/2007 | Masoud et al. | 607/60 |
| 2007/0288066 A1 * | 12/2007 | Christman et al. | 607/60 |

* cited by examiner

*Primary Examiner* — Niketa Patel
*Assistant Examiner* — Nicole F Lavert
(74) *Attorney, Agent, or Firm* — Schwegman, Lunberg & Woessner, P.A.

(57) ABSTRACT

A telemetry system is presented for enabling radio-frequency (RF) communications between implantable medical devices and an external device in a manner which increases the effective range over which such communications may take place. Devices are configured to relay communications from one device to another.

9 Claims, 3 Drawing Sheets

SYSTEM AND METHOD FOR ENABLING RELAYED COMMUNICATIONS BY IMPLANTABLE MEDICAL DEVICES

FIELD OF THE INVENTION

This invention pertains to implantable medical devices such as cardiac pacemakers and implantable cardioverter/defibrillators. In particular, the invention relates to a system and method for implementing telemetry in such devices.

BACKGROUND

Implantable medical devices (IMD's), including cardiac rhythm management devices such as pacemakers and implantable cardioverter/defibrillators, typically have the capability to communicate data with an external device (ED) via a radio-frequency telemetry link. One such external device is an external programmer used to program the operating parameters of an implanted medical device. For example, the pacing mode and other operating characteristics of a pacemaker are typically modified after implantation in this manner. Modern implantable devices also include the capability for bidirectional communication so that information can be transmitted to the programmer from the implanted device. Among the data that may typically be telemetered from an implantable device are various operating parameters and physiological data, the latter either collected in real-time or stored from previous monitoring operations.

External programmers are commonly configured to communicate with an IMD over an inductive link. Coil antennas in the external programmer and the IMD are inductively coupled so that data can be transmitted by modulating a carrier waveform which corresponds to the resonant frequency of the two coupled coils. An inductive link is a short-range communications channel requiring that the coil antenna of the external device be in close proximity to the IMD, typically within a few inches. Other types of telemetry systems may utilize far-field radio-frequency (RF) electromagnetic radiation to enable communications between an IMD and an ED over a wireless medium. Such long-range RF telemetry allows the IMD to communicate with an ED, such as an external programmer or remote monitor, without the need for close proximity.

In order for a substantial portion of the energy delivered to an antenna to be emitted as far-field radiation, the wavelength of the driving signal should not be very much larger than the length of the antenna. Far-field radio-frequency communications with an antenna of a size suitable for use in an implantable device therefore requires a carrier in the frequency range of between a few hundred MHz to a few GHz. Active transmitters and receivers for this frequency range require special RF components (typically including SiGe or GaAs semiconductor devices) that consume a significant amount of power (typically tens of milliwatts). Implantable medical devices, however, are powered by a battery contained within the housing of the device that can only supply a limited amount of continuous power before it fails. When the battery fails in an implantable device, it must be replaced which necessitates a re-implantation procedure. Power conservation is thus an important design objective in wireless telemetry systems for implantable medical devices. Due to these power considerations, as well as other factors, the range over which an IMD may communicate with an ED is limited.

SUMMARY

It is common in clinical settings for there to be multiple implantable and/or external devices present in an area. The present disclosure relates to a telemetry system for enabling radio-frequency (RF) communications between an implantable medical device and an external device in a multiple device environment in a manner that extends the effective range over which such communications may take place by utilizing the multiple devices to relay communications. In one embodiment, a first IMD is programmed to establish a communications session with a second IMD upon receipt of a relay request from an ED specifying the second IMD as the ultimate recipient. The first IMD then relays communications between the ED and the second IMD. In this way, communications between the ED and the second IMD may take place even though the ED and IMD are out their normal communications range. Access to the wireless medium among the multiple devices may be controlled by a handshaking protocol in order for a communications session between any pair of devices to be established.

DETAILED DESCRIPTION

Described herein is a telemetry system and method for enabling radio-frequency (RF) communications between an implantable medical device (IMD) and an external device (ED) in a multiple device environment which utilizes one or more non-involved devices to relay the communications between the ED and the IMD. As the term is used herein, a "non-involved" IMD is one which is not directly involved in a communications session with the ED but is available for use in retransmitting or repeating data between the ED and an IMD which would otherwise be out of range. In one embodiment, when an ED is unable to communicate with an intended IMD or has unreliable communications with it, the ED queries for other non-involved IMD's in range of the programmer. If such an IMD(s) is found, the programmer requests the non-involved IMD to attempt communication with the out of range IMD. If communication is successful, the non-involved IMD reports to the ED that communication has been established with the out of range IMD. The non-involved IMD then acts as a data repeater, passing data to and from the out of range IMD. If the non-involved IMD is unable to contact the out of range IMD, the ED may continue to ask other non-involved IMD's to attempt communication until either communication is established or communication is impossible. Further, the ED can request a non-involved IMD to query for other non involved IMD's in its range and request them to attempt communication with the out of range IMD. Thus a network of IMD's and ED's (which may be external programmers, remote monitors, or data repeaters) can be created to communicate among IMD's.

In another particular embodiment, each ED and IMD in a multiple-device environment is programmed with a relaying algorithm which allows any of the devices to respond to commands from other devices and act as data repeaters. The relaying algorithm then allows a device to receive a relay request from another device to act as a relay point, query for other non-involved devices in range of it, establish communication with other in-range devices, and retransmit data to and from the device which issued the relay request and a device which is out of range of the latter device.

The system and method as just described would be expected to be of particular use in a clinical, hospital, or patient follow-up setting where multiple IMD's, data repeaters, or external programmers are likely to be present. Set forth below are descriptions of exemplary hardware components and exemplary embodiments of a communications relaying scheme.

1. Exemplary Hardware Components

Figure 1:
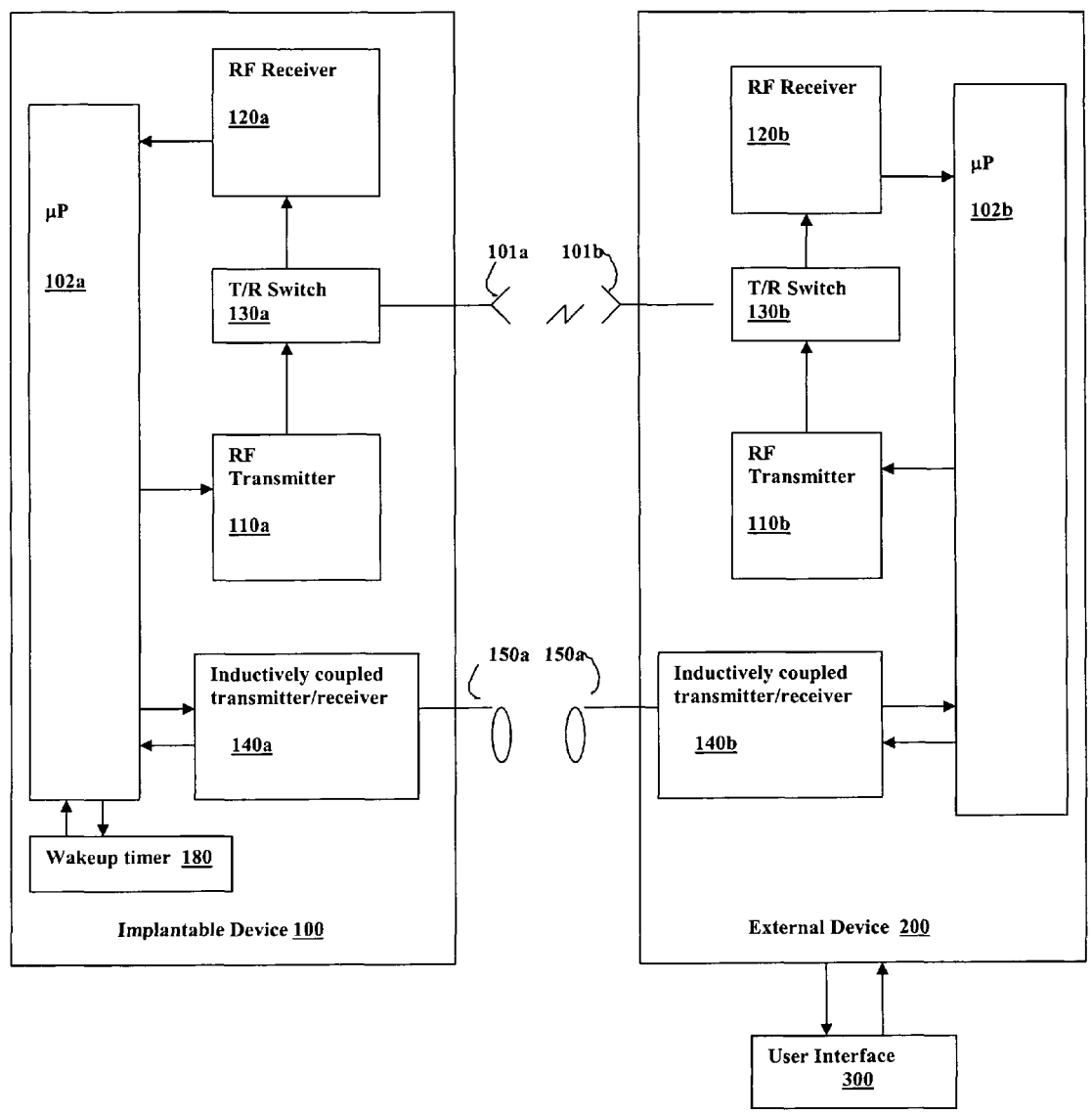
FIG. 1 is a block diagram of a telemetry system for an implantable device and an external device.

FIG. 1 shows the primary telemetry components of an external device 200 and an implantable medical device 100. In this functional block diagram, the components are shown as being identical in each device. In this exemplary embodiment, the external device and the implantable device are microprocessor-based devices each having a controller 102a or 102b that includes a microprocessor and memory for data and program storage that supervises overall device operation as well as telemetry. Code executed by the controller also implements the relaying schemes to be described below. The implantable device 100 may be a cardiac rhythm management device such as a pacemaker or implantable cardioverter/defibrillator, while the external device 200 may be an external programmer or a data-gathering device such as remote monitor. A user interface 300 (e.g., a keyboard and monitor) enables a user such as a clinician to direct the operation of the external device.

A long-range RF receiver 120a or 120b and a long-range RF transmitter 110a or 110b are interfaced to the microprocessor 102a or 102b in the implantable device and the external device, respectively. Also in each device, the transmitter and receiver are coupled to an antenna 101a or 101b through a transmit/receive switch 130a or 130b. The transmit/receive switches 130a and 130b are controlled by the microprocessor and either passes radio-frequency signals from the transmitter to the antenna or from the antenna to the receiver. To effect communications between the devices, a radio-frequency carrier signal modulated with digital data is transmitted wirelessly from one antenna to the other. A demodulator for extracting digital data from the carrier signal is incorporated into each receiver, and a modulator for modulating the carrier signal with digital data is incorporated into each transmitter. The interface to the controller for the RF transmitter and receiver in each device enables data transfer. The implantable device also incorporates a means by which the controller can power up or power down the RF receiver and/or transmitter in order to manage duty cycles. A wakeup timer 180 for defining the RF duty cycle is also shown for the implantable device, and this timer can either be implemented in code executed by the controller or can be discrete components. FIG. 1 also shows an inductively coupled transmitter/receiver 140a or 140b and antenna 150a or 150b for the implantable and external devices by which communication may take place without concern for power consumption when the two devices are in close physical proximity to one another.

2. Establishment of Communications Sessions

Figure 2:
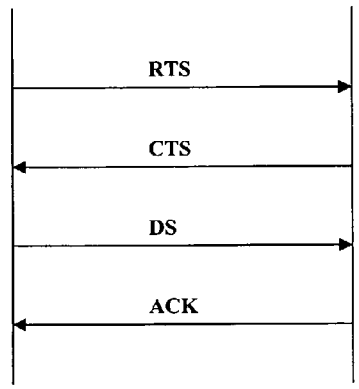
FIG. 2 illustrates a handshaking protocol for collision avoidance.

A wireless telemetry system for implantable medical devices is generally a multiple access network in which a number of network participants share the available bandwidth of the wireless medium. A medium access control (MAC) protocol may be defined which allows each network participant to acquire exclusive access to the medium before transmitting data to an intended recipient. A collision is said to occur when two or more participants attempt to transmit at the same time. In certain networks, collisions may be detected by the sender listening to the medium when a transmission is initiated to determine if other network activity is present. If a collision is detected, the sender ceases transmitting and waits for a random or defined period before trying again. Most wireless transceivers operate in a half-duplex mode, however, and cannot simultaneously transmit and listen for ongoing network activity. MAC protocols for wireless networks therefore typically use out-of-band signaling or a handshaking protocol to minimize the probability of a collision occurring. In an example of the latter type of protocol, a four-way RTS-CTS-DS-ACK exchange as illustrated by FIG. 2 is used to avoid collisions. A network participant who desires to send a message to a particular recipient first transmits a request-to-send (RTS) control frame that includes an identification code for the recipient and waits a defined period of time for a clear-to-send (CTS) control frame from the intended recipient. All other network participants who hear either of the RTS or CTS frames defer their transmissions. Upon receiving the CTS response, the sender can assume that the medium has been exclusively acquired and can then begin transmission of a data segment (DS) containing data frames to the recipient. If the data is received without errors, the recipient responds with an acknowledge (ACK) control frame which frees the medium for access by another participant. The RTS-CTS-DS-ACK frame sequence defines a communications transaction, and a communications session between two network participants may be made up of one or more such transactions.

In certain embodiments, an IMD is configured to power cycle its RF telemetry when it is not engaged in a communications session in order to conserve battery power. In such power cycling, the RF telemetry circuitry is normally in a low power state until powered up to transmit or receive a message. The controller in the IMD is programmed to maintain the RF circuitry in a quiescent or powered down state and then power up the circuitry at programmable time intervals based upon timer expirations. During the time when the RF circuitry is powered up, referred to as a wakeup window, the IMD listens for a device attempting to establish a communications session with it. An ED wishing to communicate with a power-cycled IMD may therefore have to attempt to establish communications with IMD multiple times before concluding that the device is out of range.

In other embodiments, the controllers of the external and implantable devices may be programmed to operate their respective telemetry hardware in a manner which utilizes multiple communications channels. The multiple channels are defined with different carrier frequencies so that communications over one channel does not disturb communications over any of the other channels. By using multiple channels for data transfer, a plurality of communications sessions with different implantable devices may take place simultaneously. In the case of a power cycled IMD as described above, however, it is necessary for the ED to use a channel for transmitting the initial communications transaction that is expected by the implantable device when it wakes up. A channel may therefore be dedicated to use for establishing communications with an implantable device, referred to as a control channel, with the other channels used for data communications referred to as data channels. Once a communications session is established, the ED may then find an available data channel and transmit the information to the IMD so that both devices can switch to that channel for data transfer. The control channel is then freed up for use by other devices in establishing communications sessions.

Initiation of a communications session between an ED and an IMD may thus involve a handshaking procedure as described above in which control frames are transmitted to synchronize the subsequent activity of both devices. For example, when the ED wishes to transmit data, an RTS frame is transmitted to the IMD which then responds with a CTS frame. Similarly, when the ED wishes to receive data, a request-for-request-to-send (RRTS) frame is transmitted to the IMD, the IMD responds with an RTS frame, and the ED transmits a CTS frame. One or more of the control frames may also contain other information such as the device ID, amount of data to be transmitted, and an identification of which channel is to be used for data transfer in the case of a multi-channel environment. The device receiving a CTS frame then begins transmitting data frames in the form of the data segment DS. During the data transfer, a data segment sent by one of the devices that is not acknowledged with an ACK frame is repeated in order to ensure reliable data transmission.

3. Communications Relaying

Figure 3:
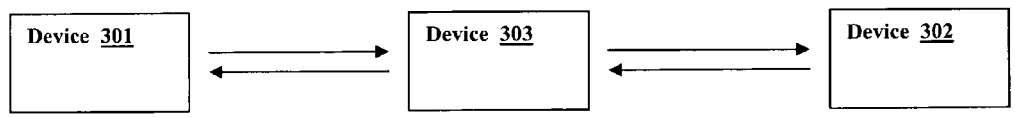
FIG. 3 illustrates an example of a relaying device configuration.

The system and method for relaying communications among devices to be described may work in the context of various types of medium access control protocols, RF power cycling, and multiple channel environments in addition to those discussed above. In an exemplary embodiment as illustrated in FIG. 3, a first device 301 (either an ED or an IMD) wants to communicate with a second device 302 (either an ED or an IMD), where the desired communication may be a data transfer or a request for data. After attempting to communicate with the second device, however, the first device concludes that the second device is out of its communications range. The first device then finds that it can communicate with a third device 303 (either an ED or an IMD) that is in communications range of the second device. The third device 303 is programmed to establish a communications session with a second device upon receipt of a relay request from a first device specifying the second device as the ultimate recipient. The third device 303 then relays the data transfer or data request from the first device to the second device. The second device may then similarly utilize the third device to relay a data transfer or data request back to the first device. Multiple devices may also be involved in relaying such communications. For example, the first device may transmit to the third device a relay request that contains a data transfer or a data request and that specifies a fourth device and the second device as the penultimate and ultimate recipients, respectively. The third device then transmits a relay request to the fourth device specifying the second device as the ultimate recipient, and the fourth device transfers the data or data request to the second device.

Figure 4:
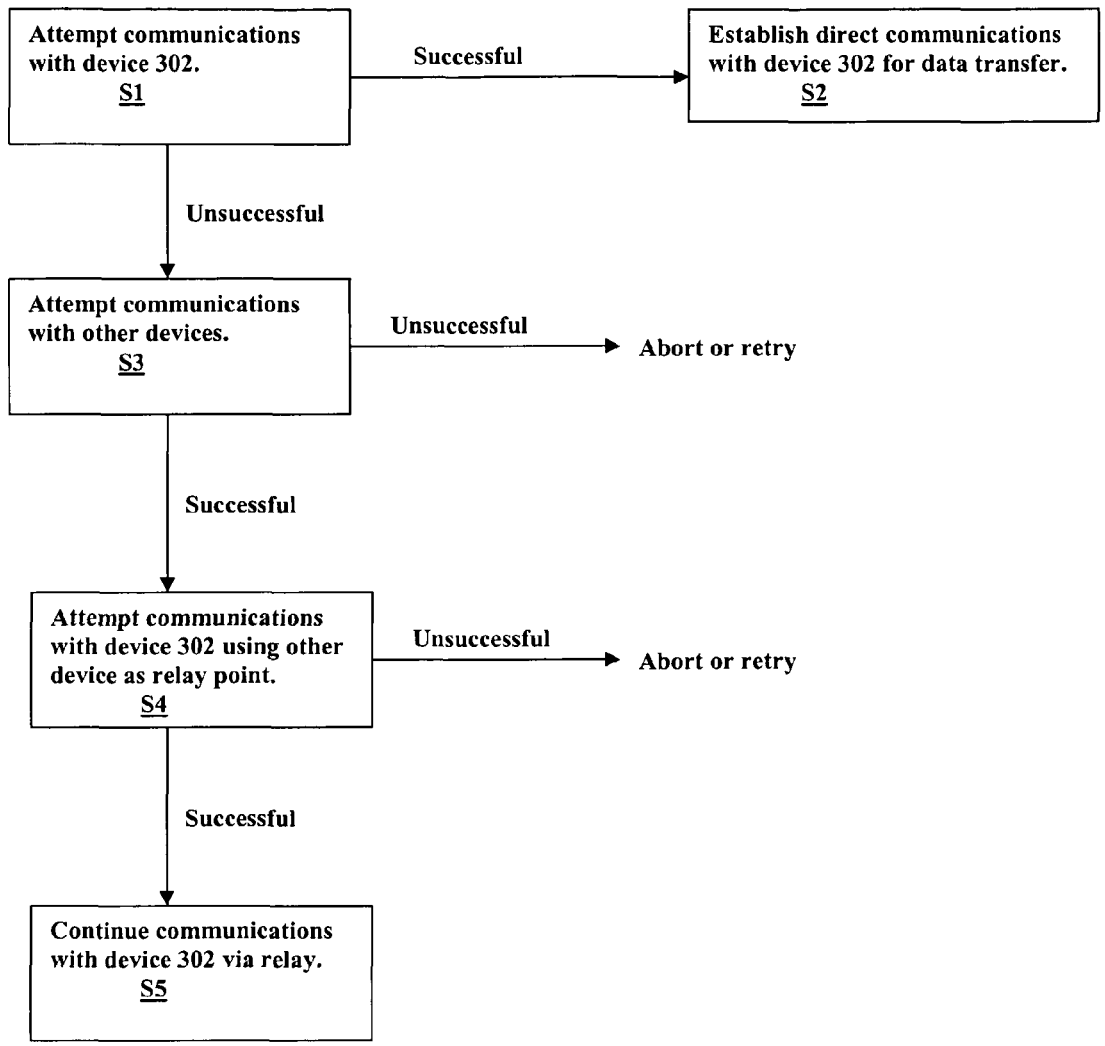
FIG. 4 illustrates an exemplary relaying algorithm.

FIG. 4 illustrates an exemplary algorithm which could be executed by the controller of an ED or IMD for implementing a communications relaying scheme as described above. At step S1, the device 301 attempts to establish a communications session with device 302 for purpose of transferring or requesting data (e.g., by transmitting a RTS or RRTS frame identifying device 302. In the case where the RF circuitry of device 302 is power cycled, this may involve multiple attempted communications transactions in order to increase the probability that the transmitted frames will occur during a wakeup window. Also, a special communications transaction may be employed for waking up a device in which special wakeup characters or a special digital key is employed. In any event, if device 302 responds (e.g., with a CTS or RTS frame), a communications session may occur directly between devices 301 and 302 at step S2. If no response from device 302 occurs, the device 301 attempts to contact device 302 via an intermediary device serving as a relay point. At step S3, device 301 attempts to communicate with other devices which might be in range. For this purpose, the devices may be programmed to transmit a device identification code upon receipt of a universal identification command from another device, where the transmitted identification code serves to identify the implantable device. In that case, device 301 would transmit the universal identification command and thereby receive identifying responses from all of the devices within its communications range. Alternatively, device 301 could try to contact individual devices in sequence according to a programmed list. If no device in range is found, the attempt to communicate with device 302 is either aborted or retried. Once at least one device in range is found, e.g., device 303, at step S4 that device is queried by device 301 to see if it can communicate with device 302. In one embodiment, device 301 queries device 303 with a request to identify other devices in communications range which then causes device 303 to transmit a universal identification command and receive identification codes from devices within communications range. Device 303 then transmits the received identification codes back to device 301. Device 301 would repeat this procedure with all of the devices within its communications range until a device is found that is within range of device 302. In another embodiment, device 301 would simply transmit a relay request to device 303 specifying device 302 as the ultimate recipient. The relay request, for example, may be contained in a data segment of a communications transaction and include the identification code of the second device. Device 303 would then attempt to establish a communications session with device 302 and transmit an indication back to device 301 whether or not the attempted communications session was successful. If neither device 303 nor any of the other devices are able to communicate with device 302, the attempt to communicate with device 302 is either aborted or retried. If device 303 or another device in range is able to communicate with device 302, a relayed communications session with device 302 is continued at step S5 until the required data transfer or data request is completed. This may involve device 302 similarly communicating with device 301 by transmitting one or more relay requests to device 303 or another device which specify device 301 as the ultimate recipient.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A telemetry system for enabling radio-frequency (RF) communications between implantable medical devices (IMD's) and an external device (ED), comprising:
   a plurality of IMD's, each IMD including an RF transmitter/receiver and a programmable controller;
   an ED including an RF transmitter/receiver and a programmable controller;
   wherein the ED is programmed to communicate with a first IMD by: 1) first attempting to establish a direct communications session with the first IMD using a handshaking protocol, 2) if the attempt at establishing a direct communications session with the first IMD is unsuccessful, querying one or more other IMD's that are within communications range as to whether the one or more other IMD's are within communications range of the first IMD, and 3) if a second IMD among the one or more other IMD's is found to be within communications range of the first IMD, transmit a request to the second IMD that the second IMD relay communications from the ED to the first IMD, referred to as a relay request; and, wherein the second IMD is programmed to relay communications between the ED and first IMD upon receiving the relay request.

2. The system of claim 1 wherein the second IMD is programmed to:

upon receiving a relay request generated by the ED, attempt to establish a communications session with the first IMD and transmit an indication back to the ED whether or not the attempted communications session was successful; and, relay communications between the ED and the first IMD if a communications session was successfully established with the first IMD.

3. The system of claim 1 wherein the IMD's are programmed to transmit a stored device identification code to the ED upon receipt of a known universal identification command from the ED, wherein the transmitted identification codes serve to identify all IMD's within communications range of the ED.

4. The system of claim 3 wherein the second IMD is programmed to:

upon receiving a request from the ED to identify other IMD's in communications range of the second IMD, transmit a universal identification command and receive identification codes from all IMD's within communications range of the second IMD; and, transmit the received identification codes to the ED.

5. The system of claim 3 wherein the ED is programmed to, if unsuccessful in establishing a direct communications session with the first IMD, transmit a universal identification command and receive identification codes from IMD's that are within range.

6. The system of claim 1 wherein the ED and the IMD's are programmed such that a communications session is effected by one of either the ED or the IMD's transmitting an RTS frame containing an identification code, receiving a CTS frame in response to the RTS frame, transmitting a data segment, and receiving an ACK frame to end the session.

7. The system of claim 6 wherein the relay request is contained in a data segment of a communications session established between the ED and the second IMD and includes the identification code of the first IMD.

8. The system of claim 7 wherein, upon receiving a relay request, the second IMD is programmed to:

establish a communications session with the first IMD and transmit data contained in the relay request to the first IMD;

receive data intended for the ED from the first IMD in a communications session established by the first IMD; and, establish a communications session with the ED to transmit data intended for the ED from the first IMD.

9. The system of claim 8 wherein the first IMD is programmed to respond to data relayed by the second IMD from the ED by establishing a communications session with the second IMD and transmitting a relay request to the second IMD specifying the ED as the ultimate recipient.

* * * * *